United States Patent [19]

Sparks et al.

[11] 4,245,636
[45] Jan. 20, 1981

[54] CONTINUOUS FLUSHING APPARATUS

[75] Inventors: Sam L. Sparks, Alpine; Gordon S. Reynolds, Bountiful, both of Utah

[73] Assignee: Sorenson Research Co., Inc., Salt Lake City, Utah

[21] Appl. No.: 6,324

[22] Filed: Jan. 24, 1979

[51] Int. Cl.[3] .................. A61M 5/00; F16K 51/00
[52] U.S. Cl. ................. 128/214 R; 128/274; 251/117
[58] Field of Search .............. 128/214 R, 214 Z, 274; 251/117; 137/238, 625.38; 138/45, 46

[56] References Cited

U.S. PATENT DOCUMENTS

| | | | |
|---|---|---|---|
| 2,864,400 | 12/1958 | Wiegel | 251/117 |
| 3,326,242 | 6/1967 | Parkison | 138/46 |
| 3,675,891 | 7/1972 | Reynolds et al. | 251/117 |
| 4,192,303 | 3/1980 | Young et al. | 128/214 R |

*Primary Examiner*—Dalton L. Truluck
*Attorney, Agent, or Firm*—H. Ross Workman; Rick D. Nydegger; J. Winslow Young

[57] ABSTRACT

An apparatus for providing continuous flushing of intravascular catheters. The apparatus consists of a small block having passages which define a continuously open path through which flushing solution is introduced into a catheter. A flow resistor is placed in the continuously open path in order to limit the flushing solution to a desired small amount. At least a portion of the block consists of a resilient sleeve which surrounds the flow resistor. The resilient sleeve provides a by-pass passage around the flow resistor. A disk placed in the by-pass passage cooperates with the resilient sleeve selectively opened to permit relatively large amounts of flushing solution to be introduced into the catheter when desired.

8 Claims, 10 Drawing Figures

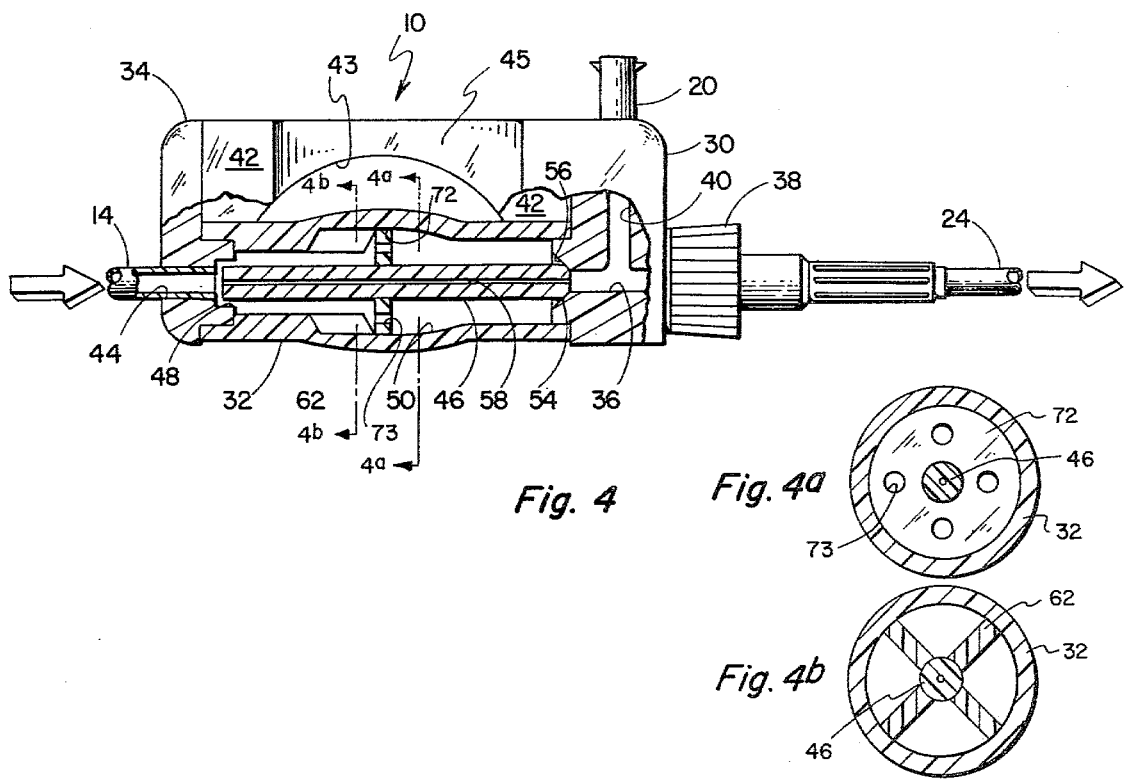
*Fig. 4*  *Fig. 4a*  *Fig. 4b*
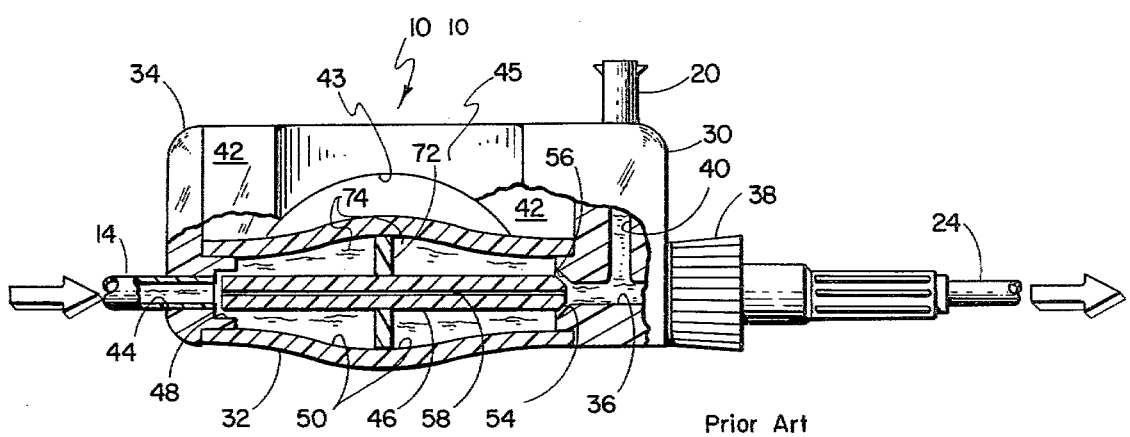
Prior Art
*Fig. 5*

CONTINUOUS FLUSHING APPARATUS

BACKGROUND

1. Field of the Invention

The present invention relates to intravascular catheter systems for monitoring physiological phenomena, for example, blood pressure in various regions of the heart, and in particular the present invention relates to an apparatus for effecting continuous flushing of such intravascular catheter systems.

2. The Prior Art

Catheter cannulation of an artery or a vein for pressure monitoring has long been recognized as an important technique for monitoring conditions in the thoracic cavity both during and after surgery. Such monitoring systems can provide valuable information pertaining to heart rate, stroke volume, cardiac output, duration of systole, and systolic, diastolic and mean blood pressures.

However, in order to insure a high quality clinical recording of central arterial pulse waveforms, it has been found necessary to continuously flush the catheter to prevent occlusion of the catheter end by clotting blood. In many instances such monitoring systems may be required to operate continuously over a period of several days, and it is thus essential to prevent occlusion of the catheter end by clotted blood.

Various types of continuous catheter flushing systems have theretofore been developed. An example of one type of system is illustrated and described in U.S. Pat. No. 3,581,733. In this type of system, a saline flushing solution is conducted through a long capillary tube which limits the amount of flushing solution passed through the catheter system to a predetermined small amount. A larger by-pass tube is also provided which may be used to quickly prime the system with the saline solution. A stopcock is provided with this tubing system so as to direct the flushing solution through either the large by-pass tube or through the long, narrow capillary tube.

One disadvantage of this type of system is that it is complicated to set up, requiring several connections to stopcocks and tubing. Moreover, the use of stopcocks in the system results in a decrease of the pressure pulse fidelity because of minute leaks in the stopcocks.

More recently, continuous catheter flushing devices have been devised which eliminate the complicated tubing and use of stopcocks described above. One such device is illustrated in U.S. Pat. No. 3,675,891. Another prior art device consists of a small unitary piece of apparatus which may be connected directly into the tubing of the catheter system. This type of device is sufficiently light in its weight that it may be suspended by the tubing. An example of one such type of prior art device is illustrated in FIG. 5 below.

However, even with the improved continuous catheter flushing device illustrated in FIG. 5, inaccuracies in the recorded pressure pulses have persisted. One reason for these inaccuracies is that the extremely sensitive pressure monitoring equipment will sense and will reflect any damping of the pressure pulses caused by the continuous catheter flushing apparatus.

Accordingly, what is needed is an improved continuous catheter flushing apparatus which incorporates the advantages of small size and efficient operation but which also maximizes the fidelity of the recorded pressure pulses by minimizing the damping effects otherwise created by the continuous catheter flushing device. Such an invention is disclosed and claimed herein.

BRIEF SUMMARY AND OBJECTS OF THE INVENTION

The present invention consists of a small, unitary, lightweight continuous catheter flushing device. The device consists of a block having passages therein which provide a continuously open path through which a flushing solution may be introduced into the catheter system. A capillary tube is placed in the continuously open path in order to limit the amount of solution being introduced into the catheter to approximately three cubic centimeters per hour. The capillary tube is surrounded by a resilient sleeve. The space between the capillary tube and the resilient sleeve forms a by-pass around the capillary tube. A small disk interposed between the capillary tube and resilient sleeve cooperates with the resilient sleeve to function as a resilient valve so that the by-pass passage may be selectively opened in order to permit relatively large quantities of flushing solution to be quickly passed through to the catheter system for purposes of priming the system or checking pressure monitoring equipment.

In one embodiment of the invention, the damping effects otherwise created by the resilient sleeve are minimized by placing a spring in the resilient sleeve. The spring engages the disk that is attached to the capillary tube and forces the outlet end of the capillary tube tightly against the outlet portion of the continuously open passage which communicates with the capillary tube.

In a second embodiment of the invention, the damping effects of the resilient sleeve are eliminated by providing an annular shoulder about the inside periphery of the resilient sleeve. The annular shoulder abuts the disk that is joined to the capillary tube and forces the outlet end of the capillary tube tightly against the outlet portion of the continuously open passage as will be hereinafter more fully described.

It is therefore a primary object of the present invention to provide a small, lightweight, unitary continuous catheter flushing apparatus which is so constructed as to eliminate the use of all stopcocks in a flushing system.

Another object of the present invention is to provide a continuous catheter flushing apparatus having a capillary tube which limits the amount of flushing solution continuously introduced into the catheter system to a predetermined small amount, typically on the order of three cubic centimeters per hour.

Another object of the present invention is to provide a continuous catheter flushing apparatus that may be quickly actuated to provide a by-pass around the capillary tube so as to introduce relatively large amounts of flushing solution into the catheter system for purposes of priming the system or for testing the dynamics of the pressure transducer system.

A further object of the present invention is to minimize the damping effect of the continuous catheter flushing apparatus.

These and other objects and features of the present invention will become more fully apparent from the following description and appended claims taken in conjunction with the accompanying drawing.

BRIEF DESCRIPTION OF THE DRAWING

FIG. 4 is an enlarged central vertical cross sectional view of a second embodiment of the present invention.

FIG. 4a is a front elevation of one preferred disk configuration used in the embodiment of FIG. 4.

FIG. 4b is a cross sectional view taken along lines 4b—4b of FIG. 4.

FIG. 5 is an enlarged sectional view illustrating a prior art continuous catheter flushing device.

DETAILED DESCRIPTION OF THE PREFERRED EMBODIMENTS

Figure 1:
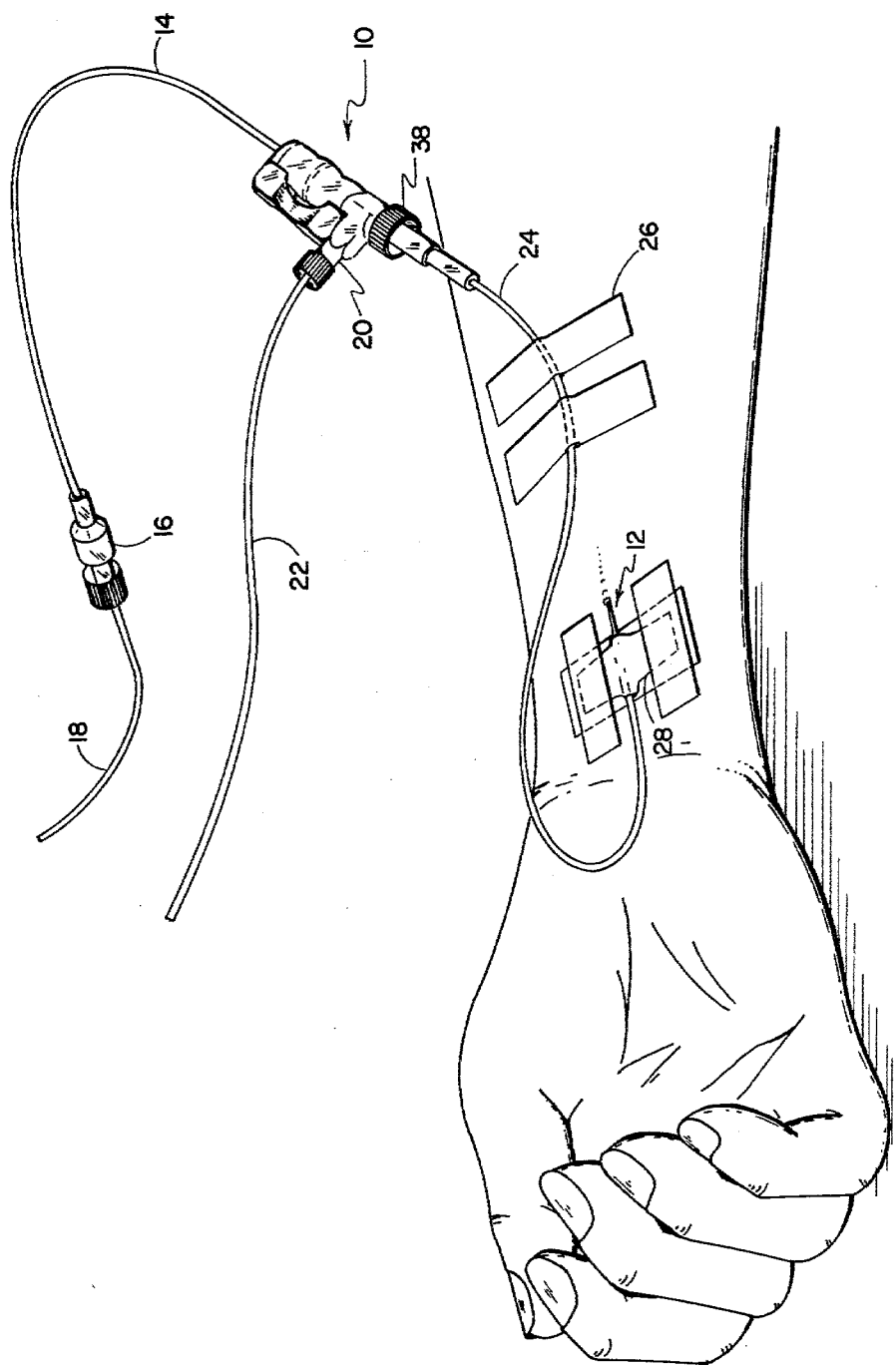
FIG. 1 is a schematic illustration of one presently preferred embodiment of the continuous catheter flushing apparatus of the present invention in operative association with a cannulated patient.

Reference is now made to the drawing wherein like parts have like numerals throughout.

The continuous catheter flushing apparatus of the present invention may be used in various types of catheter systems for the purpose of preventing the formation of a blood clot or other occlusion at the distal end of a catheter. In particular, the continuous catheter flushing apparatus is highly useful in systems for monitoring venous and arterial pressures.

By way of example, the continuous catheter flushing apparatus generally designated 10 in FIG. 1 is shown and described herein in operative association with a catheter system generally designated 12 introduced into the radial artery of a patient for the purpose of monitoring central arterial pressure. Typically the catheter 12 used in such a system is a thin catheter with an inside diameter of approximately one-half millimeter.

At the inlet end of the continuous catheter flushing apparatus 10, a tube 14 is connected through a luer fitting 16 to the tubing 18 of a conventional source of sterile saline solution. A valve (not shown) on the tubing 18 is used to increase the fluid source pressure to approximately 300 millimeters of mercury. An in-line filter (not shown) may also be provided so as to eliminate any micro-particles which may otherwise plug the device 10.

The continuous catheter flushing device 10 is also attached through a conventional luer fitting 20 to the tubing 22 of a pressure transducer system (not shown). The transducer system permits clinical recording of central arterial pulse waveforms on an occilloscope, strip chart or other such recording media.

As further illustrated in FIG. 1, the outlet end of the continuous catheter flushing device 10 is attached through a luer fitting 38 to the tubing 24 of catheter 12. Typically, tubing 24 is taped to the arm of the patient as illustrated at 26 and 28 so as to minimize movement of the tubing 24 which in turn minimizes trauma to the artery into which the distal end of the catheter has been inserted.

The continuous catheter flushing apparatus 10 is adapted to be connected directly into the tubing 14, 22 and 24 and is sufficiently small and light in weight so as to permit suspension of the apparatus 10 by the tubing.

Experience has shown that a small amount of saline solution must be continuously passed through the catheter 12 in order to prevent the formation of blood clots or other occlusions. Based upon current preferred practice, approximately 1 cc of infusion solution per hour is preferred for infants. In the case of an adult, 2-3 cc per hour of solution is presently preferred. Some practitioners prefer infusion rates of as much as 6 cc per hour and clearly, the preferred infusion rates recited herein are illustrative only.

In addition to the continuous infusion of saline solution to the catheter system, the entire system must be rapidly flushed in the first instance to clear the system of air and to fill the system with the saline solution. A rapid flush is also necessary from time to time to check the dynamics of the transducer system, as more particularly described below.

Figure 2:
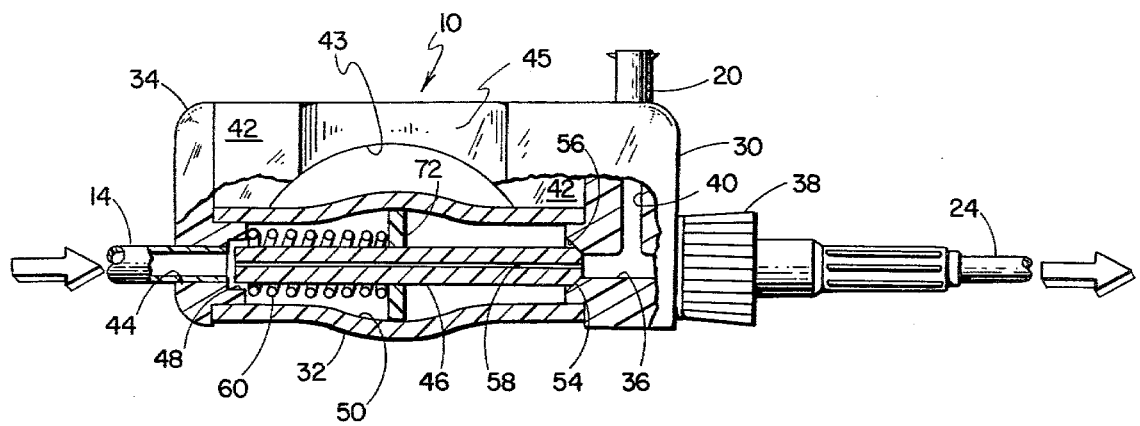
FIG. 2 is an enlarged central vertical cross sectional view of the device illustrated in FIG. 1, with the resilient valve shown in a closed position.

The continuous catheter flushing apparatus 10 is more particularly illustrated in FIG. 2. The apparatus 10 may be fabricated from parts molded of rigid plastic material, preferably transparent, and the various parts are cemented together by fusing or with the use of a solvent, or in any other suitable manner.

As shown in FIG. 2, the apparatus consists of a small unitary block that is composed of a body 30, a resilient sleeve 32 and an end cap 34.

Body 30 is molded to provide a continuously open outlet passage 36 which terminates in a conventional female luer fitting 38, to which the tubing 24 of the catheter system 12 may be attached. Another passage 40 is in fluid communication with the continuously open outlet passage 36 and extends vertically upwardly so as to terminate in a male luer fitting 20. As described above, the male luer fitting 20 is adapted to be attached to the tubing 22 (see FIG. 1) of a transducer system (not shown) for purposes of monitoring central arterial pressure through the passage 40. Passage 40 may also be used for purposes of hypodermic injections.

The sides 42 of the body 30 are constructed so as to form an arch 43 over the central portion of the resilient sleeve 32. As more fully described below, the arching configuration of sides 42 accommodates squeezing of the resilient sleeve 32 when it is desired to rapidly flush the catheter system. Sides 42 may also be inwardly tapered at 45 toward the top of the arch to improve finger access of the resilient sleeve 32 for purposes to be hereinafter more fully described. The space between sides 42 is hollow so that the overall weight of the apparatus 10 will be very light.

End cap 34 is joined to the body 30 at the inlet end of the apparatus 10. End cap 34 is molded so as to provide a continuously open inlet passage 44 which receives the tubing 14.

A flow resistor in the form of a capillary tube 46 is placed between the continuously open inlet and outlet passages 44 and 36. The inlet end of the capillary tube 46 is placed within a diametrally enlarged bore 48 provided in the inlet passage 44. As hereinafter more fully described, the diametrally enlarged bore 48 in inlet passage 44 provides fluid communication with a by-pass passage 50 formed by the space between the capillary tube 46 and the resilient sleeve 32 which surrounds the capillary tube 46. The by-pass passage 50 is of a size that will permit a relatively large amount of infusion fluid to be rapidly flushed through the catheter system 12.

The outlet end of capillary tube 46 is seated within a conically shaped bore 56 that is provided in the continuously open outlet passage 36. The outlet end of the capillary tube 46 is slightly bevelled as at 54 so as to permit the capillary tube 46 to be tightly seated against the conically shaped bore 56. As more fully described below, the outlet end of capillary tube 46 must be tightly seated against the bore 56 in order to prevent damping of the central arterial pulse waveforms that are being monitored. The outlet end of capillary tube 46 must be unseated, however, when it is desired to rapidly flush the catheter system.

The capillary tube 46 passes through a rigid disk 72 that is joined to the capillary tube 46 at approximately the center thereof. The radius of disk 72 is slightly larger than the inside radius of the resilient sleeve 32 so that disk 72 will forcefully seat against the sleeve 32, causing a slight bulge at the center of sleeve 32.

Sleeve 32 is constructed from silastic or any other suitable type of highly resilient material. Thus, as described more fully below, resilient sleeve 32 will, in cooperation with disk 72, function as a resilient valve for purposes of selectively by-passing the capillary tube 46.

The bore 58 provided through the capillary tube 46 is but several hundredeths of a millimeter in diameter so as to afford a high resistance to the flow of infusion solution through the tube 46. It will of course be appreciated that the bore 58 has been exaggerated in the drawing for the purpose of clarity since otherwise the bore 58 is so small as to be almost invisible to the naked eye when gazing at the end of the tube 46. It will further be appreciated that small variations in the radius of the bore 58 may be provided in order to vary the amount of the flow.

In determining the amount of flushing solution that will flow through the continuous catheter flushing device 10, the resistances of the catheter 12 (FIG. 1) and associated tubing and filter (not shown) must be taken into consideration. These resistances may readily be determined and they may then be used to accurately determine the size of the bore 58 which will provide the desired flow rate of approximately 3 cubic centimeters per hour.

Experience has shown that back pressure from the patient's body has no adverse effect on the flow, and the flow rate of about 3 cubic centimeters per hour will constantly flush the catheter to avoid any occlusion therein. Moreover, a flow rate of about 3 cubic centimeters per hour will not interfere or lessen the quality of the clinical recording of central arterial pulse waveforms.

As further illustrated in FIG. 2, spring 60 is positioned inside the resilient sleeve 32. Spring 60 exerts a force against the disk 72 that is attached to capillary tube 46. The force exerted on disk 72 causes the outlet end of the capillary tube 46 to be tightly seated against bore 56.

The importance of providing the spring 60 so as to insure that the capillary tube 46 remains tightly seated at the outlet passage 36 can best be appreciated by comparing the structure of the prior art device illustrated in FIG. 5. As shown in FIG. 5, without spring 60 the outlet end of capillary tube 46 is not tightly seated within the bore 56. Thus, there is fluid communication between the outlet passage 36 and the space 50 between the capillary tube 46 and resilient sleeve 32.

Figure 6:
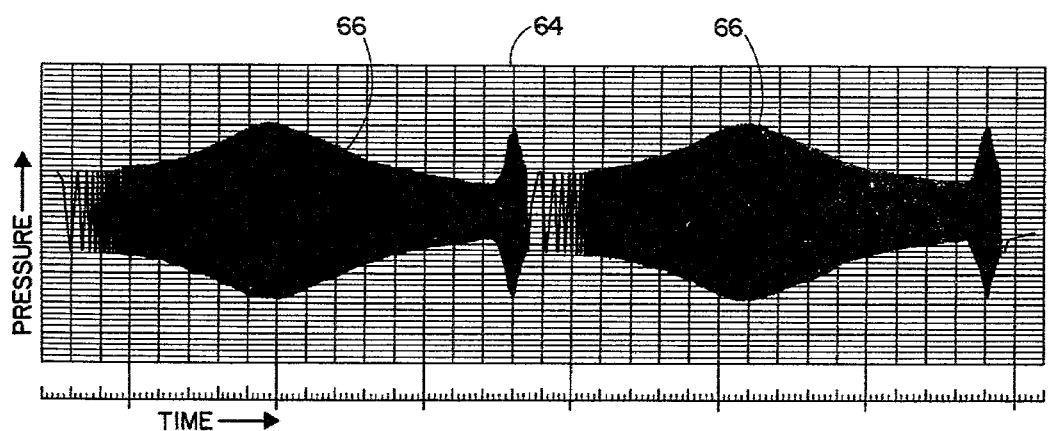
FIG. 6 illustrates a recording of undistorted pressure pulses on a graph.
Figure 7:
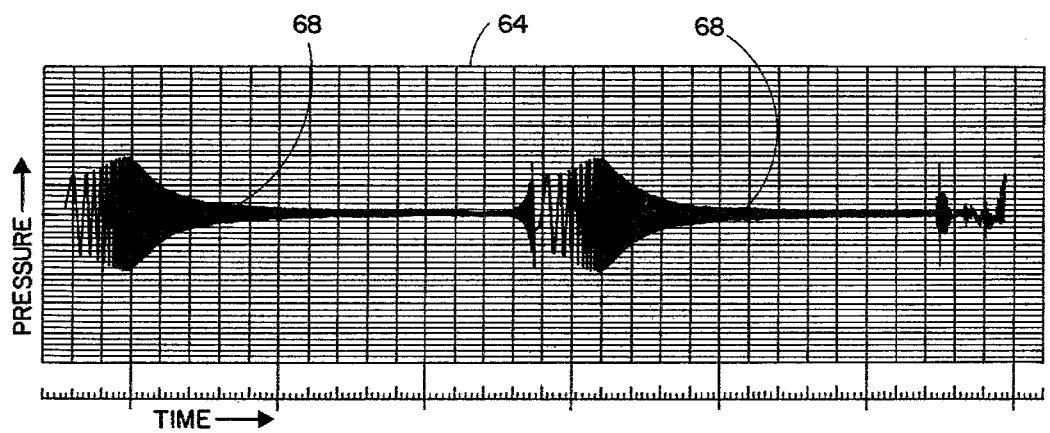
FIG. 7 illustrates a recording of pressure pulses on a graph where the recording has been distorted by damping created by a continuous catheter flushing device.

Since resilient sleeve 32 is made of silastic or other highly resilient material, pressure pulse waveforms will be communicated throughout the fluid 74 contained in outlet passage 36 and space 50 of the prior art device, and will be severly damped by the resilient sleeve 32. FIG. 7 illustrates the pressure pulse waveforms 68 that are recorded utilizing the prior art device of FIG. 5. The undistorted waveforms 66 recorded in the absence of a continuous monitoring device are illustrated in FIG. 6. Clearly, the waveforms recorded with the prior art device are highly distorted in comparison to the undistorted pressure pulse waveforms 66 as illustrated in FIG. 6. In fact, the critical features are obscured beyond recognition.

Figure 8:
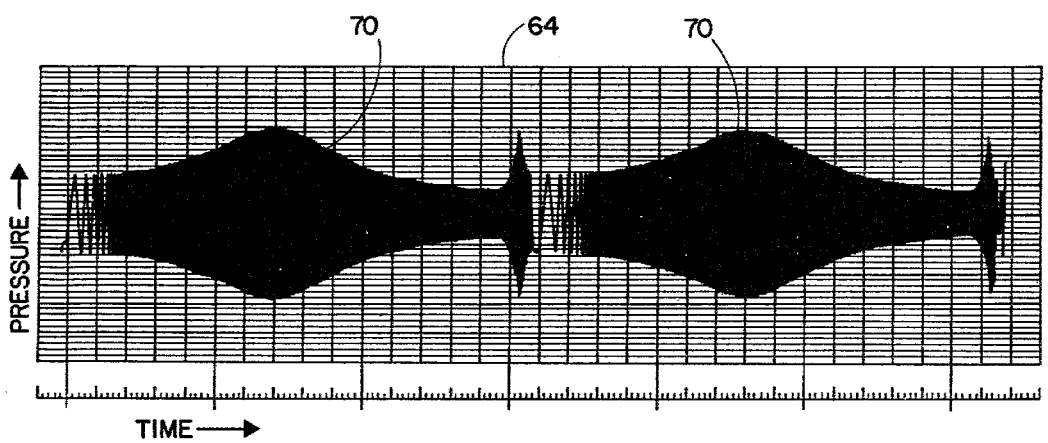
FIG. 8 illustrates a recording on a graph of pressure pulses monitored through the continuous catheter flushing apparatus of the present invention, showing the elimination of distortions due to damping.

By providing spring 60 so as to cause the outlet end of capillary tube 46 to be tightly seated within bore 56, the damping effect of the resilient sleeve 32 is essentially eliminated since there is no fluid communication between the space 50 and the outlet passage 36. FIG. 8 illustrates pressure pulse waveforms 70 recorded on a continuous catheter flushing device like that illustrated in FIG. 2. The waveforms of FIG. 8 show little, if any, distortion by virtue of the damping that would otherwise be caused by the prior art device of FIG. 5.

Figure 3:
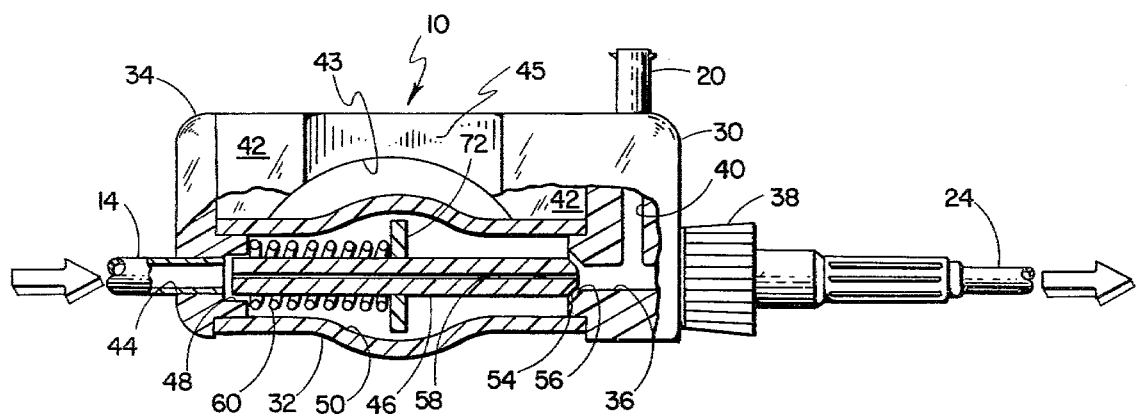
FIG. 3 is an enlarged central vertical cross sectional view of the device of FIG. 1, with the resilient valve shown in an open position.

Referring now to FIG. 3, the manner of operating the continuous catheter flushing device 10 so as to rapidly flush the catheter system may readily be seen. In order to rapidly flush the system, the resilient sleeve 32 is pinched at the point which corresponds to the disk 72. At the same time, the disk 72 is pulled back slightly against the spring 60 so as to unseat the outlet end of the capillary tube 46 from the bore 56. As resilient sleeve 32 is pinched, the seal at the upper and lower portions of the disk 72 is broken permitting fluid to flow around the disk 72 through by-pass passage 50 and into the outlet passage 36. In order to terminate the rapid flush of the system, it is only necessary to release the resilient sleeve 32. Sleeve 32 will then automatically seat against the disk 72 and the spring 60 will urge the outlet end of the capillary tube 46 back into seating engagement with the bore 56 of outlet passage 36.

It will thus be appreciated that disk 72 cooperates with the resilient sleeve 50 so as to function as a resilient valve which may instantaneously and automatically close the by-pass passage 50.

The rapid flushing procedure described above may be used to advantage when it is desired to prime the system or when it is desired to check the dynamics of the transducer system. For example, a rapid flush of saline solution will cause a square wave to appear on an oscilloscope or recording graph. The appearance of the square wave will not mislead the observer nor will it confuse any permanent recording since it is easily distinguishable.

Moreover, when using the continuous catheter flushing apparatus 10, there will be no backflow because the blood pressure of the patient is insufficient to force liquid through the capillary tube 46 in the reverse direction. The apparatus is extremely light in weight. The block consisting of body 30, silastic sleeve 32, and end cap 34, exclusive of the luer fittings, typically is on the order of seven eights inch (2.22 cm) long, three quarters of an inch (1.91 cm) wide and one quarter of an inch (0.64 cm) thick.

The apparatus of the present invention is highly efficient as to its functioning and eliminates complicated interconnections of tubing with stopcocks, and makes it possible to monitor the central arterial pulse waveform with its various perameters with ease and flexibility. The apparatus is sufficiently economical to warrant its disposal along with the catheter after single usage, if such is desired, although the device may be sterilized after its use and may thereafter be used again.

Reference is now made to FIG. 4 which illustrates a second embodiment of the present invention. The embodiment illustrated in FIG. 4 is in all respects identical to that previously described in connection with FIGS. 2 and 3 except for the manner in which the capillary tube 46 is maintained in seating engagement with the bore 56 of outlet passage 36.

As shown in FIG. 4, rather than using a spring, a small annular shoulder 62 is provided at spaced intervals about the inside periphery of the resilient sleeve 32. The annular shoulder 62 abuts against the disk 72 and is provided at a point along the length of resilient sleeve 32 such that a spring-like action will be developed by the resiliency of the sleeve 32. The spring-like action created by shoulder 62 will forcefully seat the outlet end of capillary tube 46 against the bore 56 of outlet passage 36. If desired, disk 72 may be provided with apertures 73 which facilitate communication of fluid beyond the disk 72 for improved fast flush.

The operation of the continuous catheter flushing device illustrated in FIG. 4 is essentially like that of FIG. 2. In order to rapidly flush the system, the user applies a squeezing force at the sides of the resilient sleeve 32 opposite the disk 72 and at the same time pulls disk 72 slightly back so as to unseat the capillary tube 46 from bore 56. This action will break the seal around the outside periphery of disk 72 thus opening the by-pass passage 50 so as to permit fluid to flow therethrough and into the outlet passage 36. When the resilient sleeve 32 is released, disk 72 will automatically and instantanously close the by-pass passage 50 and the outlet end of capillary tube 46 will again be seated against the bore 56.

The invention may be embodied in other specific forms without departing from its spirit or essential characteristics. The described embodiment is to be considered in all respects only as illustrative and not restrictive and the scope of the invention is, therefore, indicated by the appended claims rather than by the foregoing description. All claims that come within the meaning and range of equivalency of the claims are to be embraced within their scope.

What is claimed and desired to be secured by a United States Letters Patent is:

1. A continuous catheter flushing apparatus comprising:
    a block having passages therein that define a continuously open inlet-outlet path through said block;
    a flow resistor in the form of a capillary tube placed in said continuously open path to limit the flow therethrough of liquid under pressure to a desired minimum amount;
    at least a portion of said block comprising a resilient sleeve which surrounds said capillary tube, the space between said resilient sleeve and said capillary tube forming a by-pass passage around the part of said continuously open inlet-outlet path containing said flow resistor, and said by-pass passage having a size sufficient to permit a fast flow of liquid therethrough;
    valve means positioned in the by-pass passage of said resilient sleeve and so mounted as to forcefully seat against said sleeve, said valve means cooperating with said resilient sleeve so as to automatically and instantaneously close said by-pass passage when said resilient sleeve is released; and
    means for maintaining the outlet end of said capillary tube tightly seated within the outlet portion of said continuously open path whenever said by-pass passage is closed by said valve means.

2. The apparatus of claim 1 wherein said block is essentially less than one inch (2.54 centimeters) in any direction and sufficiently light in weight as to permit suspension in a fluid line.

3. An apparatus as defined in claim 1 further comprising a flexible tube connected to said block at the inlet end of said continuously open path and a fitting on the other end of said flexible tube for connection to a pressurized fluid source.

4. The apparatus of claim 1 wherein said block has a monitoring passage therethrough with one end of said monitoring passage in fluid communication with the outlet portion of said continuously open path, and a fitting at the other end of said monitoring passage for connection to monitoring means or to be plugged for hypodermic injection.

5. The apparatus of claim 1 wherein said flow resistor is sized to permit a flow of approximately three cubic centimeters per hour.

6. An apparatus as defined in claim 1 wherein said valve means comprise a disk joined to said capillary tube and interposed between said capillary tube and said resilient sleeve.

7. An apparatus as defined in claim 6 wherein said means for maintaining the outlet end of said capillary tube tightly seated within the outlet portion of said continuously open path comprises a spring positioned in said resilient sleeve so as to exert a force against the disk that is joined to said capillary tube, thereby urging the outlet end of said capillary tube against the outlet portion of said continuously open path.

8. An apparatus as defined in claim 6 wherein said means for maintaining the outlet end of said capillary tube tightly seated within the outlet portion of said continuously open path comprises and annular shoulder formed about the inside periphery of said resilient sleeve, said annular shoulder being formed at a position along the length of said sleeve so as to abut the disk that is joined to said capillary tube, thereby urging the outlet end of said capillary tube against the outlet portion of said continuously open path.

* * * * *